(12) United States Patent
Fournie

(10) Patent No.: US 7,955,317 B2
(45) Date of Patent: Jun. 7, 2011

(54) FEMALE ADAPTOR FOR FEEDING LINE

(75) Inventor: Glenn Fournie, Smithton, IL (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/495,335

(22) Filed: Jun. 30, 2009

(65) Prior Publication Data

US 2010/0331787 A1    Dec. 30, 2010

(51) Int. Cl.
*A61M 25/16* (2006.01)
(52) U.S. Cl. ....................................................... 604/533
(58) Field of Classification Search .......... 604/533–539; 251/149.9, 89.5
See application file for complete search history.

(56) References Cited

U.S. PATENT DOCUMENTS

| | | |
|---|---|---|
| 4,326,516 A | 4/1982 | Schultz et al. |
| 4,354,492 A | 10/1982 | McPhee |
| 4,388,076 A | 6/1983 | Waters |
| 4,390,017 A | 6/1983 | Harrison et al. |
| 4,405,316 A | 9/1983 | Mittleman |
| 4,636,200 A | 1/1987 | Vaillancourt |
| 4,790,832 A | 12/1988 | Lopez |
| 4,840,614 A | 6/1989 | Maaz |
| 4,895,562 A | 1/1990 | Lopez |
| 4,950,254 A | 8/1990 | Andersen et al. |
| 5,057,093 A | 10/1991 | Clegg et al. |
| 5,125,893 A | 6/1992 | Dryden |
| 5,137,527 A | 8/1992 | Miller et al. |
| 5,199,947 A | 4/1993 | Lopez et al. |
| 5,215,538 A | 6/1993 | Larkin |
| 5,234,417 A | 8/1993 | Parks et al. |
| 5,242,429 A | 9/1993 | Nwaneri et al. |
| 5,250,040 A | 10/1993 | Parks et al. |
| 5,267,983 A | 12/1993 | Oilschlager et al. |
| 5,269,771 A | 12/1993 | Thomas et al. |
| 5,273,523 A | 12/1993 | Sozuki et al. |
| 5,344,414 A | 9/1994 | Lopez et al. |
| 5,399,173 A | 3/1995 | Parks et al. |
| 5,437,650 A | 8/1995 | Larkin et al. |
| 5,460,603 A | 10/1995 | DeSantis |
| 5,507,733 A | 4/1996 | Larkin et al. |
| 5,533,983 A | 7/1996 | Haining |
| 5,569,222 A | 10/1996 | Haselhorst et al. |
| 5,637,102 A | 6/1997 | Tolkoff et al. |
| 5,645,538 A | 7/1997 | Richmond |
| 5,665,064 A | 9/1997 | Bodicky et al. |

(Continued)

FOREIGN PATENT DOCUMENTS

WO    0139827 A1    6/2001

*Primary Examiner* — Kevin C Sirmons
*Assistant Examiner* — Deanna K Hall

(57) ABSTRACT

An adaptor for discriminating connection of an oral tip having a length greater than 0.50 (12.70 mm) to a feeding line and for preventing sealed connection with a standard semi-rigid luer tip having a length less than or equal to 0.50 in (12.70 mm) is disclosed. The adaptor includes a duckbill valve spaced at least 0.50 in (12.70 mm) downstream from a first open end of the body such that when an oral tip is fully inserted into a connection port, the oral tip engages valve flaps of the duckbill valve and opens the valve, and when a standard semi-rigid luer tip is fully inserted into the connection port, the standard semi-rigid luer tip does not contact the valve flaps and the valve flaps remain in a closed position.

20 Claims, 9 Drawing Sheets

U.S. PATENT DOCUMENTS

| | | | |
|---|---|---|---|
| 5,688,254 A | 11/1997 | Lopez et al. | |
| 5,776,116 A | 7/1998 | Lopez et al. | |
| 5,797,897 A | 8/1998 | Jepson et al. | |
| 5,820,614 A | 10/1998 | Erskine et al. | |
| 5,836,924 A | 11/1998 | Kelliher et al. | |
| 5,848,997 A | 12/1998 | Erskine et al. | |
| 5,871,500 A | 2/1999 | Jepson et al. | |
| 5,954,708 A | 9/1999 | Lopez et al. | |
| 5,971,950 A | 10/1999 | Lopez et al. | |
| 6,113,572 A | 9/2000 | Gailey et al. | |
| 6,146,374 A * | 11/2000 | Erskine et al. | 604/533 |
| 6,165,168 A | 12/2000 | Russo | |
| 6,183,465 B1 * | 2/2001 | Meier et al. | 604/535 |
| 6,217,568 B1 | 4/2001 | Jepson et al. | |
| 6,290,688 B1 | 9/2001 | Lopez et al. | |
| 6,423,053 B1 | 7/2002 | Lee | |
| 6,722,705 B2 | 4/2004 | Korkor | |
| 6,786,879 B1 | 9/2004 | Bolam et al. | |
| 6,786,887 B2 | 9/2004 | Roychowdhury et al. | |
| 6,808,521 B1 | 10/2004 | McMichael | |
| 6,811,139 B2 | 11/2004 | Hishikawa | |
| 6,908,449 B2 | 6/2005 | Willis et al. | |
| 7,063,690 B2 | 6/2006 | Kessler et al. | |
| 7,080,672 B2 | 7/2006 | Fournie et al. | |
| 2002/0013715 A1 | 1/2002 | Yoshinaga et al. | |
| 2002/0198502 A1 | 12/2002 | Vohsing | |
| 2003/0109848 A1 | 6/2003 | Fleeman | |
| 2003/0216713 A1 | 11/2003 | Kessler et al. | |
| 2004/0044330 A1 | 3/2004 | Li et al. | |
| 2004/0158229 A1 | 8/2004 | Quinn | |
| 2005/0033267 A1 | 2/2005 | Decaria | |
| 2005/0033268 A1 | 2/2005 | Decaria | |
| 2005/0033269 A1 | 2/2005 | Decaria | |
| 2006/0047251 A1 | 3/2006 | Bickford Smith et al. | |
| 2007/0076401 A1 | 4/2007 | Carrez et al. | |
| 2008/0228125 A1 | 9/2008 | Brugger et al. | |

* cited by examiner

_FEMALE ADAPTOR FOR FEEDING LINE_

FIELD OF THE INVENTION

The present invention generally relates to a female adaptor for a feeding line.

BACKGROUND OF THE INVENTION

Tubing and catheter misconnections are a serious problem in hospitals. One such type of misconnection error involves enteral feeding tubes and intravenous catheters. Enteral feeding tubes are used to administer liquid nutritional solutions and medications directly to a patient's gastrointestinal system. In contrast, intravenous catheters are used to administer liquid nutritional solutions and medications directly to a patient's vascular system. Patients may be harmed if feeding solutions are administered intravenously and vice versa. Errors such as this occur because medical professionals use similar or identical tubing for different purposes. The use of luer tips, including luer-lock components, contributes to many of these errors because they enable functionally dissimilar tubes or catheters to be connected. For example, a luer tip may be inserted improperly into a connector or adaptor of a feeding tube, with potential harmful results.

SUMMARY OF THE INVENTION

In one aspect, an adaptor for discriminating connection of an oral tip having a length greater than 0.50 (12.70 mm) to a feeding line and for preventing sealed connection with a standard semi-rigid luer tip having a length less than or equal to 0.50 in (12.70 mm) generally comprises a body having first and second open ends and a passage for flow of fluid from the first end to the second end. An oral tip connector defines a connection port in the passage adjacent the first end of the body. The connection port is sized and shaped to sealingly receive the oral tip and to prevent sealing connection with the standard semi-rigid luer tip having a length less than or equal to 0.50 in (12.70 mm). A duckbill valve is in the passage between the first and second open ends of the body. The duckbill valve comprises valve flaps that are biased toward a closed position in which the flaps are in sealing contact with one another at an apex of the valve to substantially seal the second open end of the body from the connection port. The duckbill valve is spaced at least 0.50 in (12.70 mm) downstream from the first open end of the body such that when the oral tip is fully inserted into the connection port, the oral tip engages the valve flaps and opens the valve. When the standard semi-rigid luer tip is fully inserted into the connection port, the standard semi-rigid luer tip does not contact the valve flaps and the valve flaps remain in the closed position.

In another aspect, a feeding administration set generally comprises an oral tip having a length greater than 0.50 in (12.70 mm). An adaptor comprises a body having first and second open ends and a passage for flow of fluid from the first end to the second end. An oral tip connector defines a connection port in the passage adjacent the first end of the body. The connection port is sized and shaped to sealingly receive the oral tip. A duckbill valve is in the passage between the first and second open ends of the body. The duckbill valve comprises valve flaps that are biased toward a closed position in which the flaps are in sealing contact with one another at an apex of the valve to substantially seal the second open end of the body from the connection port. The duckbill valve is spaced downstream from the first open end of the body such that when the oral tip is fully inserted into the connection port, the oral tip engages the valve flaps and opens the valve.

In yet another aspect, an adaptor for connecting an oral tip to a feeding line generally comprises a tubular body having an exterior surface. First and second open ends and a passage for flow of fluid from the first end to the second end. An integrally formed, one-piece oral tip connector is secured to the body. The oral tip connector includes an inner sealing member in the passage adjacent the first end of the body defining a connection port that is and shaped to sealingly receive the oral tip. The inner sealing member has first and second ends, a skirt having a radial portion adjacent the first end of the sealing member and overlying the first open end of the body, and an axial portion surrounding the exterior surface of the body. A duckbill valve adjacent the second end of the inner sealing member is in the passage between the first and second open ends of the body. The duckbill valve comprises valve flaps that are biased toward a closed position in which the flaps are in sealing contact with one another at an apex of the valve to substantially seal the second open end of the body from the connection port. The duckbill valve is spaced downstream from the first open end of the body such that when the oral tip is fully inserted into the connection port, the oral tip contacts the valve flaps and opens the valve.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
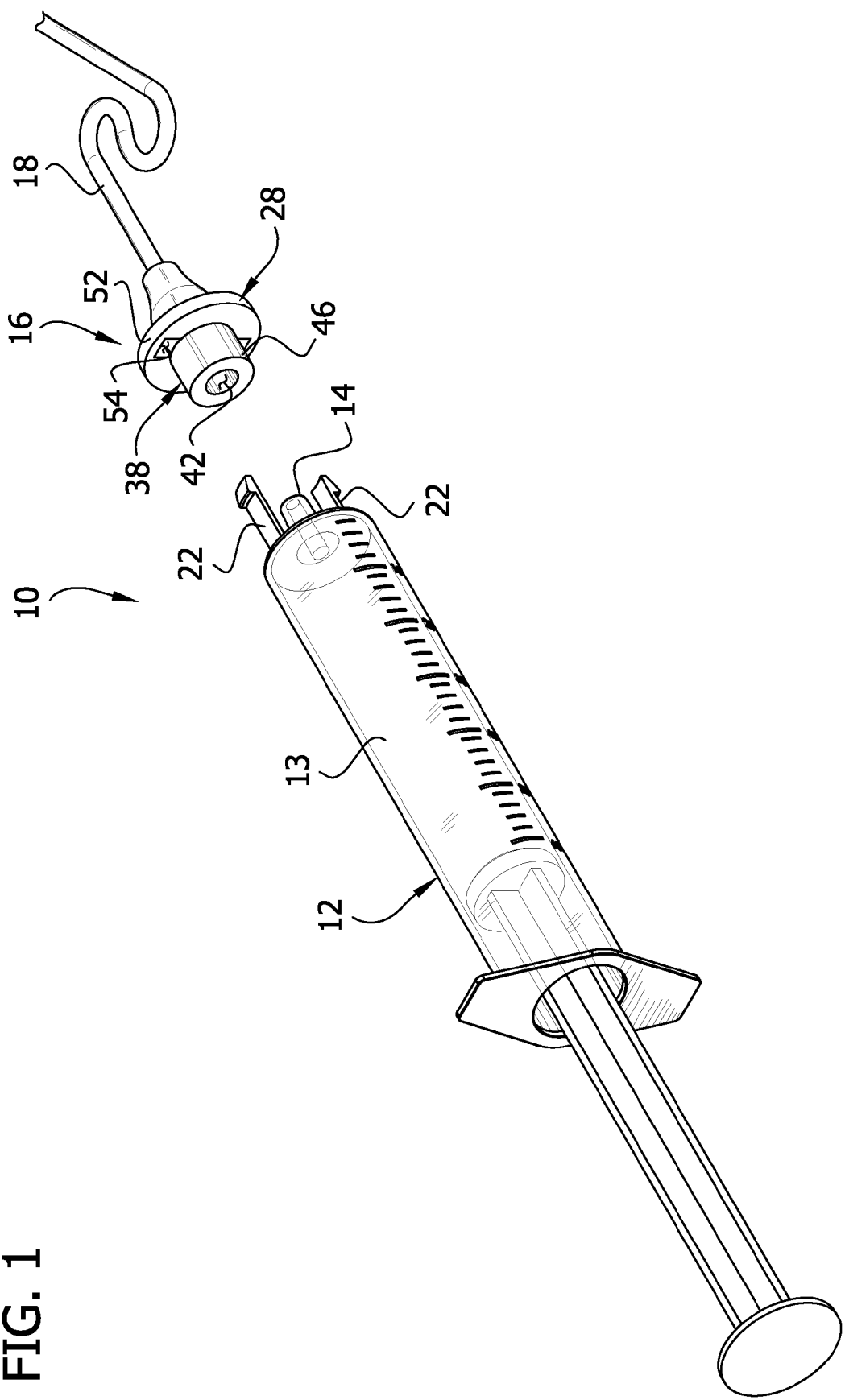
FIG. 1 is a perspective of one embodiment of an enteral feeding set.
Figure 1A:
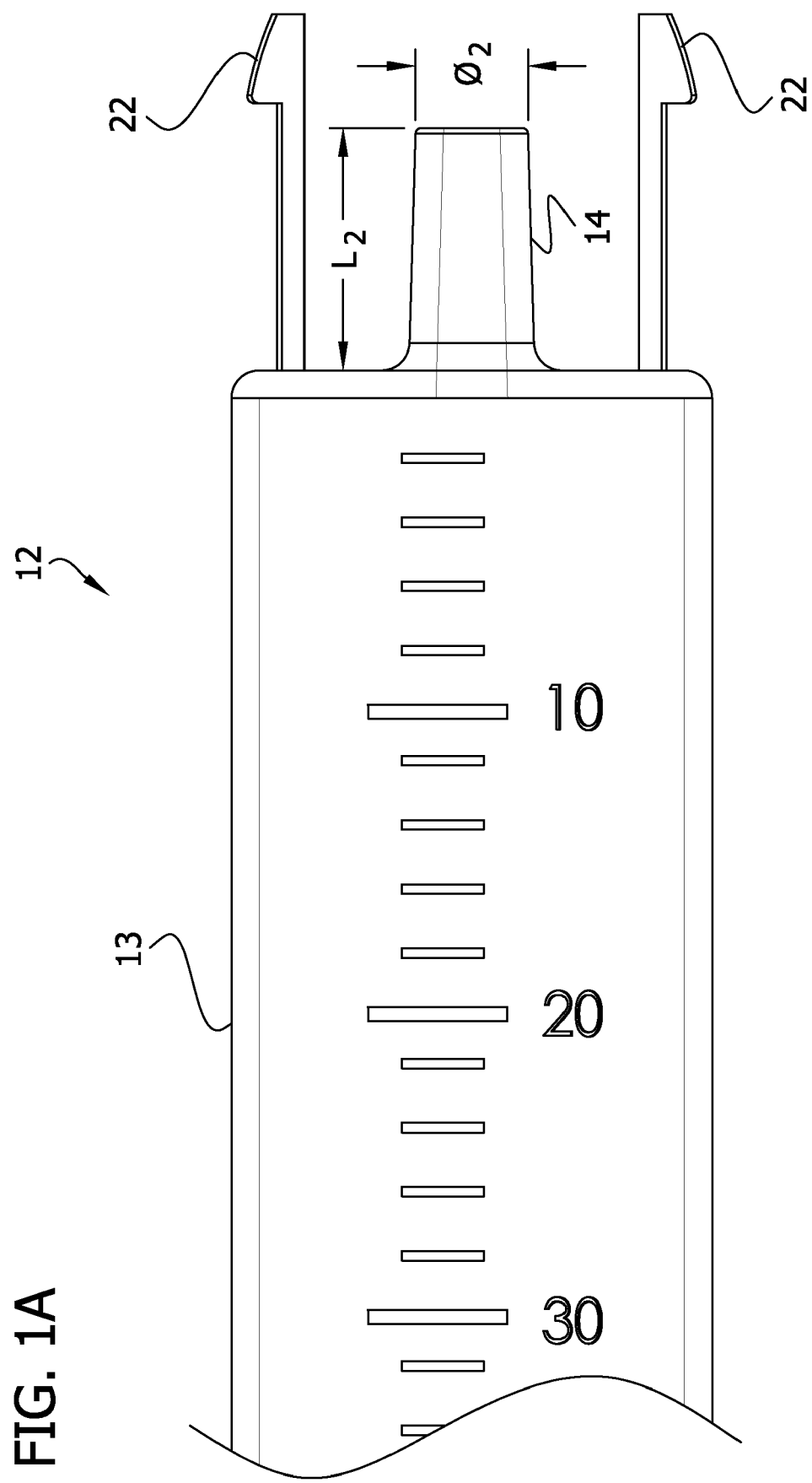
FIG. 1A is an enlarged, fragmentary side elevation of an oral tip syringe of the feeding set.
Figure 2:
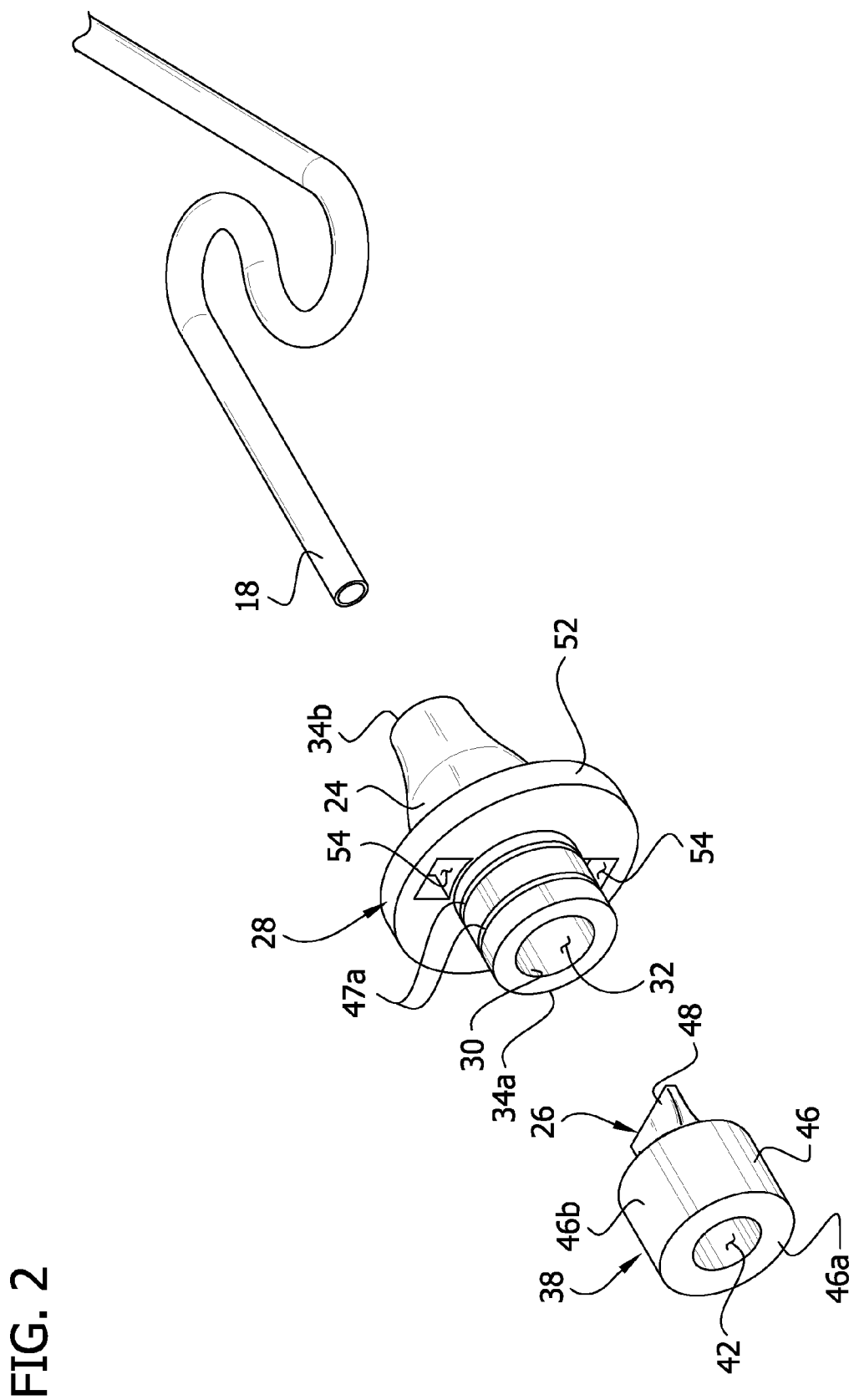
FIG. 2 is an exploded perspective of a female adaptor and feeding tube of the enteral feeding set.
Figure 6:
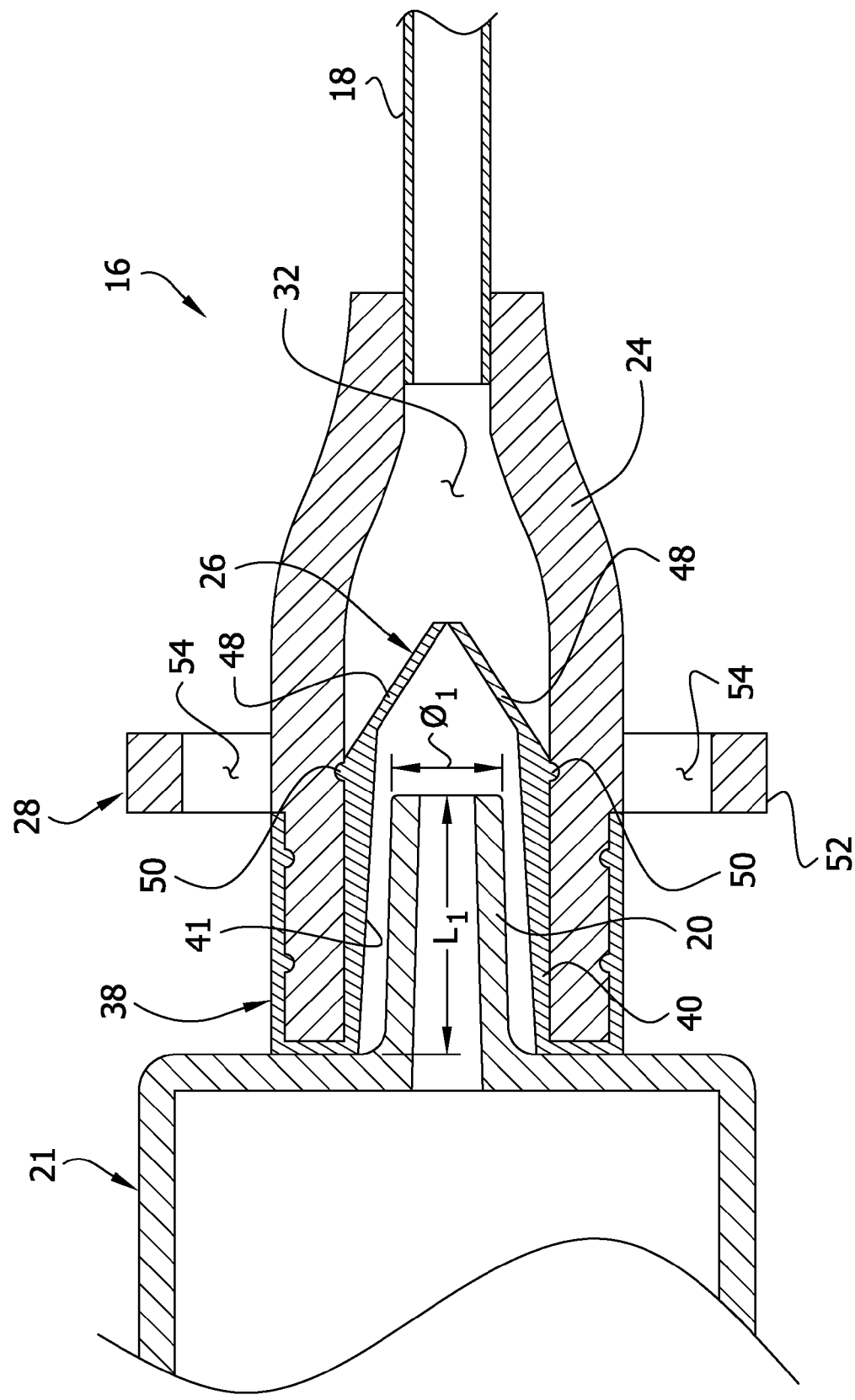
FIG. 6 is a sectional view of the female adaptor similar to FIG. 5 but with a standard semi-rigid luer tip syringe inserted in the female adaptor.

Referring to FIG. 1, an enteral feeding set is generally indicated at 10. The enteral feeding set includes a syringe (broadly, a source of liquid enteral product), generally indicated at 12, comprising a barrel 13 and an oral tip 14 extending outward from the barrel. The feeding set 10 also includes a female adaptor, generally indicated at 16, secured to a feeding line comprising feeding tubing 18. The female adaptor 16 is compatible with the oral tip 14 of the syringe 12 for delivering the liquid enteral product into the feeding tubing 18 and to a patient. Specifically, the adaptor 16 is configured for permitting connection of the oral tip 14 to the feeding line 18 and for preventing connection of a standard semi-rigid luer tip to the feeding line, as shown in FIG. 6. As defined herein, a standard semi-rigid luer tip, such as semi-rigid luer tip 20 of syringe 21 in FIG. 6, has specifications as given by the International Organization for Standardization (ISO) in ISO 594-1:1986 and 594-2:1998, including a 6% taper and an outer cross-sectional diameter $\varnothing_1$ (FIG. 6) at the free end of the tip measuring between about 3.925 mm (0.154 in) and about 4.027 mm (0.159 in) for semi-rigid material. A length $L_1$ (FIG. 6) of the semi-rigid standard luer tip 20 is not standardized. However, the lengths $L_1$ of most, if not all, types and brands of standard semi-rigid luer tips 20 that are presently on the market are less than or equal to 0.50 in (12.70 mm). In the illustrated embodiment, the free end of the oral tip 14 has an outer cross-sectional diameter $\varnothing_2$ (FIG. 1A) that is greater than the maximum cross-sectional diameter $\varnothing_1$ of the free end of the standard semi-rigid luer tip 20. For example, the outer cross-sectional diameter $\varnothing_2$ of the free end of the oral tip 14 may measure within a range of 5.10 mm (0.201 in) to 5.15 mm (0.203 in). Also in the illustrated embodiment, a length $L_2$ (FIG. 1A) of the oral tip 14 is greater than 0.50 in (12.70 mm). For example, the length $L_2$ of the oral tip 14 may measure within a range of 16.50 mm (0.65 in) to 17.50 mm (0.69 in). For reasons explained below, male snap-fit components 22 extend outward from the syringe 12 generally parallel to the oral tip 14.

Figure 3:
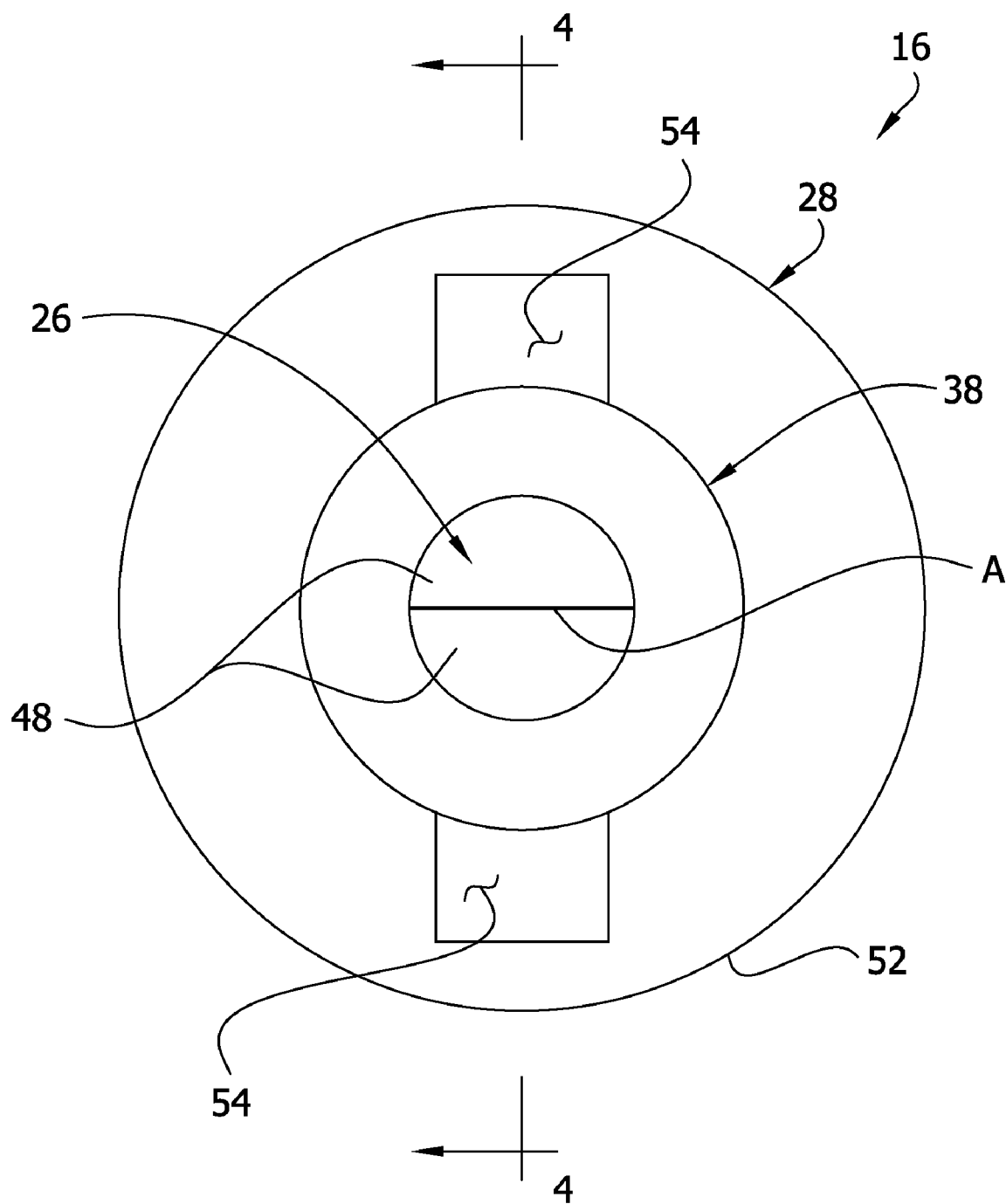
FIG. 3 is a front elevation of the female adaptor.
Figure 4:
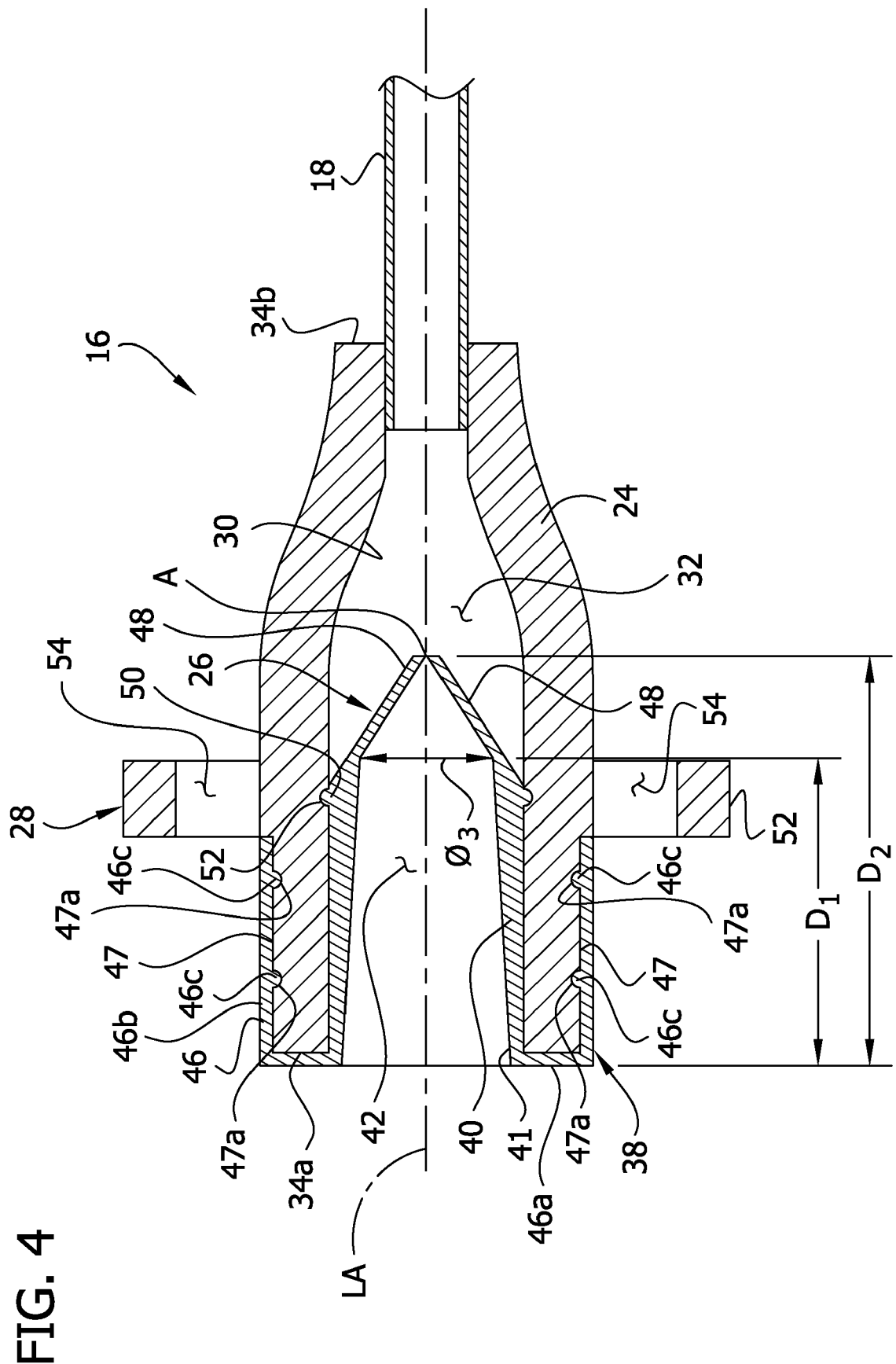
FIG. 4 is a sectional view of the female adaptor taken in the plane including the line 4-4 in FIG. 3.

Referring to FIGS. 2-5, the female adaptor 16 generally comprises a tubular body 24, an internal duckbill valve, generally indicated at 26, and a female snap-fit component 28. In one embodiment, the tubular body 24 is generally rigid and may be formed from a rigid plastic, such as PVC. Alternatively, the body 24 may be formed from other material. Referring to FIGS. 3 and 4, the tubular body 24 has an interior surface 30 defining a passage 32 that extends between opposite first and second open ends 34a, 34b, respectively, of the body. A cross-sectional diameter of the interior surface 30 tapers toward the second open end 34b of the body 24. The interior surface 30 adjacent to the second open end 34b of the tubular body 24 is sized and shaped to axially receive an end portion of the feeding tubing 18 (as shown in FIG. 4) and to retain the tube therein by friction-fit connection and/or by adhesive. Other ways of securing the female adaptor 16 to the tubing 18 are within the scope of the invention.

In the illustrated embodiment, an oral tip connector, generally indicated at 38, is secured to the tubular body 24 at the first open end 34a. The oral tip connector 38 includes a tubular inner sealing member 40 extending into the tubular body 24 from the first open end 34a of the body, The inner sealing member 40 has an interior surface 41 defining a connection port 42 that sealingly receives the oral tip 14 of the syringe 12 to prevent leakage when liquid is delivered into the adaptor 12 via the syringe. In the illustrated embodiment, the oral tip connector 38 and the duckbill valve 26 are integrally formed as a one-piece, connector-valve component. The duckbill valve 26 is integrally formed at an end of the inner sealing member 40 located inside the passage 32 of the adaptor body 24. In one example, the inner sealing member 40 and the duckbill valve 26 are generally elastically deformable, and may be made from rubber or other elastic materials. It is contemplated that the oral tip connector 38 may be formed integrally with the interior surface 30 of the passage 32 without departing from the scope of the present invention. In such an embodiment, the duckbill valve 26 may be secured to or otherwise extend from (e.g., integrally formed with) the interior surface 30 of the passage. Other configurations are within the scope of the invention.

In the illustrated embodiment, the oral tip connector 38 also includes an outer member or skirt 46 formed integrally with the inner sealing member 40. The skirt 46 has a radial portion 46a which overlies the first open end 34a of the tubular body 24 and an axial portion 46b surrounding an exterior surface of the adaptor body 24. The axial portion 46b of the skirt 46 is received in an annular recess 47 in the exterior surface of the adaptor body 24 so that an outer surface of the skirt is generally flush with the exterior surface of the body adjacent the recess. Spaced apart outer O-rings 46c on an inner surface of the axial portion 46b of the skirt 46 are received in annular grooves 47a in the exterior surface of the body 24. The O-rings 46c are secured within the grooves by adhesive, or they may be secured in other ways. It is understood that the skirt 46 may be formed separately from the port liner 40 and secured thereto. It is also understood that the oral tip connector 38 may not include the skirt 46 without departing from the scope of the present invention. Moreover, the oral tip connector 38 and the tubular body 24 may be integrally formed as a single, one-piece component without departing from the scope of the invention.

Referring to FIGS. 2-5, the duckbill valve 26 includes generally elastic valve flaps 48 extending radially inward toward a central longitudinal axis LA of the opening 42 of the connection port 38. The flaps 48 are biased to a closed position in which the flaps are in sealing contact with one another at an apex A of the duckbill valve 26 (see FIG. 4). In the closed position, the flaps 48 form a seal that closes the corresponding end of the connection port 42 and prevents fluid communication between the connection port 42 and the feeding tubing 18. As explained below, the valve flaps 48 are hinged at the end of the inner sealing member 40 and open when the oral tip 14 is fully inserted into the connector port to a position contacting the flaps (see FIG. 5). An inner O-ring 50, generally proximate to the duckbill valve 26, is received in an annular recess 52 in the interior surface 30 of the body 24 to form a fluid-tight seal between the inner sealing member 40 and the interior surface 30 of the tubular body 24. In the illustrated embodiment, the inner O-ring 50 is formed integrally with the oral tip connector 38, although it may be formed separately without departing from the scope of the present invention. The O-ring 50 may be secured within the annular groove 52 using adhesive, or it may be secured in other ways.

Figure 5:
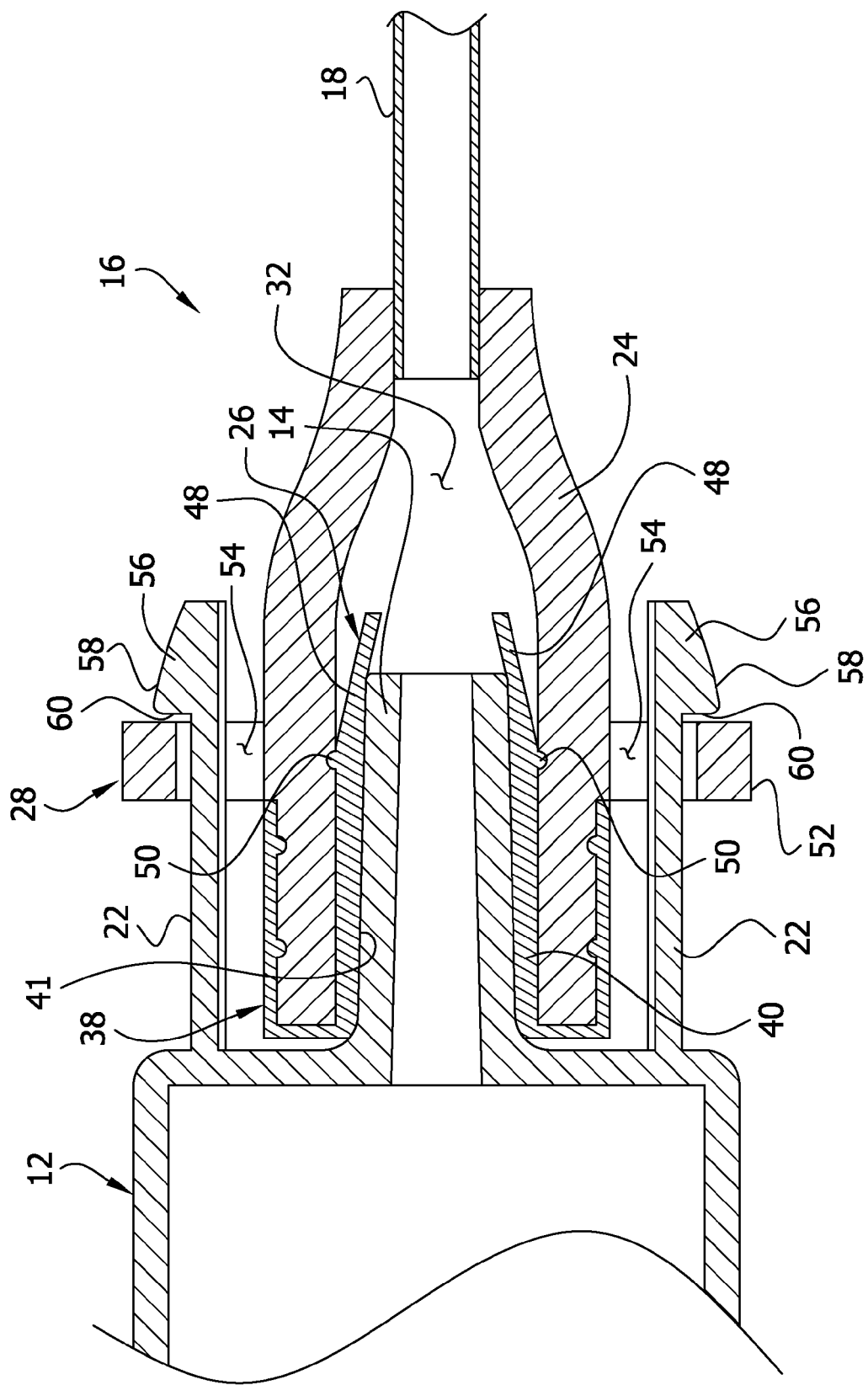
FIG. 5 is similar to FIG. 4 but with the oral tip syringe of the enteral feeding set inserted in the female adaptor.

Referring to FIG. 5, the inner sealing member 40 and the duckbill valve 26 are sized and shaped so that when the oral tip 14 is fully inserted into the port 42, the oral tip both seals with the interior surface 41 of the inner sealing member and contacts the valve flaps 48 to open the duckbill valve. Moreover, as shown in FIG. 6, the inner sealing member 40 is sized and shaped so that when the standard semi-rigid luer tip 20 is inserted into the port 42, the standard semi-rigid luer tip will not seal with the interior surface 41 of the inner sealing member.

In one example, the port 42 of the oral tip connector 38 has a 6% taper toward the valve 26 and the end of the port adjacent to the valve has a minimum cross-sectional diameter $\varnothing_3$ greater than 4.027 mm (0.159 in), which is the maximum outer diameter $\varnothing_1$ of the free end of the standard semi-rigid luer tip 20. In one example, the end of the port 42 adjacent to the valve 26 has a cross-sectional diameter $\varnothing_3$ in a range of about 5.10 mm (0.201 in) to 5.15 mm (0.203 in). In other examples, the cross-sectional diameter is in the range of about 4.32 mm (0.170 in) to about 5.59 mm (0.220 in), or in the range of about 4.83 mm (0.190 in) to about 5.33 in (0.210 mm). Further, the duckbill valve 26 may be spaced from the open end of the port 42 a distance $D_1$ greater than about 12.70 mm (0.50 in). In one example, the distance $D_1$ may be greater than 12.70 mm (0.50 in) and less than or equal to about 25.4 mm (1.0 in), and more particularly, greater than 12.70 mm (0.50 in) and less than or equal to about 19.1 mm (0.75 in). It is believed that this distance $D_1$ is of sufficient magnitude to prevent most, if not all, types and brands of standard semi-rigid luer tips that are presently on the market from contacting and opening the duckbill valve 26. In addition, a distance $D_2$ extending from the open end of the port 42 to the apex A of the duckbill valve 26 may measure between about 15.50 mm (0.61 in) and about 16.00 mm (0.63 in).

In the illustrated embodiment, the female snap-fit component 28 of the female adaptor 16 includes a circumferential flange 52 on the tubular body 24 with opposite first and second planar faces lying in planes that are generally transverse to the axis LA of the connection port opening 42. As illustrated, the flange 52 is generally circular, but it may have other configurations (e.g., generally oblong). Diametrically opposing openings 54 extend through the flange 52. The openings 54 are sized, shaped and located on the flange 52 to receive the respective male snap-fit components 22 extending longitudinally outward from the oral-tip syringe 12 to form a snap-fit connection. The male snap-fit components 22 are generally elongate and elastically bendable or deflectable along their lengths and include barbs 56 adjacent their respective free ends. Outer surfaces 58 of the barbs 56 taper toward the free ends of the snap-fit components 22 to facilitate insertion of the barbs into respective openings 54 of the female snap-fit component 28. Upon insertion of the barbs 56 in respective openings 54, the male snap-fit components 22 elastically deflect radially inward, toward the oral tip 14. Substantially simultaneously, the oral tip 14 enters the connection port 38. When the barbs 56 of the male snap-fit components 22 pass completely through the respective openings 54 in the female snap-fit component 28, the male-components spring or rebound back to their original, relaxed configuration. Engagement surfaces 60 (e.g., 90 degree edges) prevent unintended disconnection of the syringe 12 from the adaptor 16 because the engagement surfaces will contact the female snap-fit component 28 and will not pass through the openings 54. The syringe 12 can be disconnected from the adaptor 16 by inwardly deflecting (e.g., squeezing) the barbs 56 of the male snap-fit components 22 to allow the barbs to pass through the openings 54 when the syringe 12 is withdrawn from the port 42. Other types of connections are within the scope of the invention. Moreover, the syringe or feeding device and the adaptor 16 may not have mateable connectors within the scope of the invention.

Figure 7:
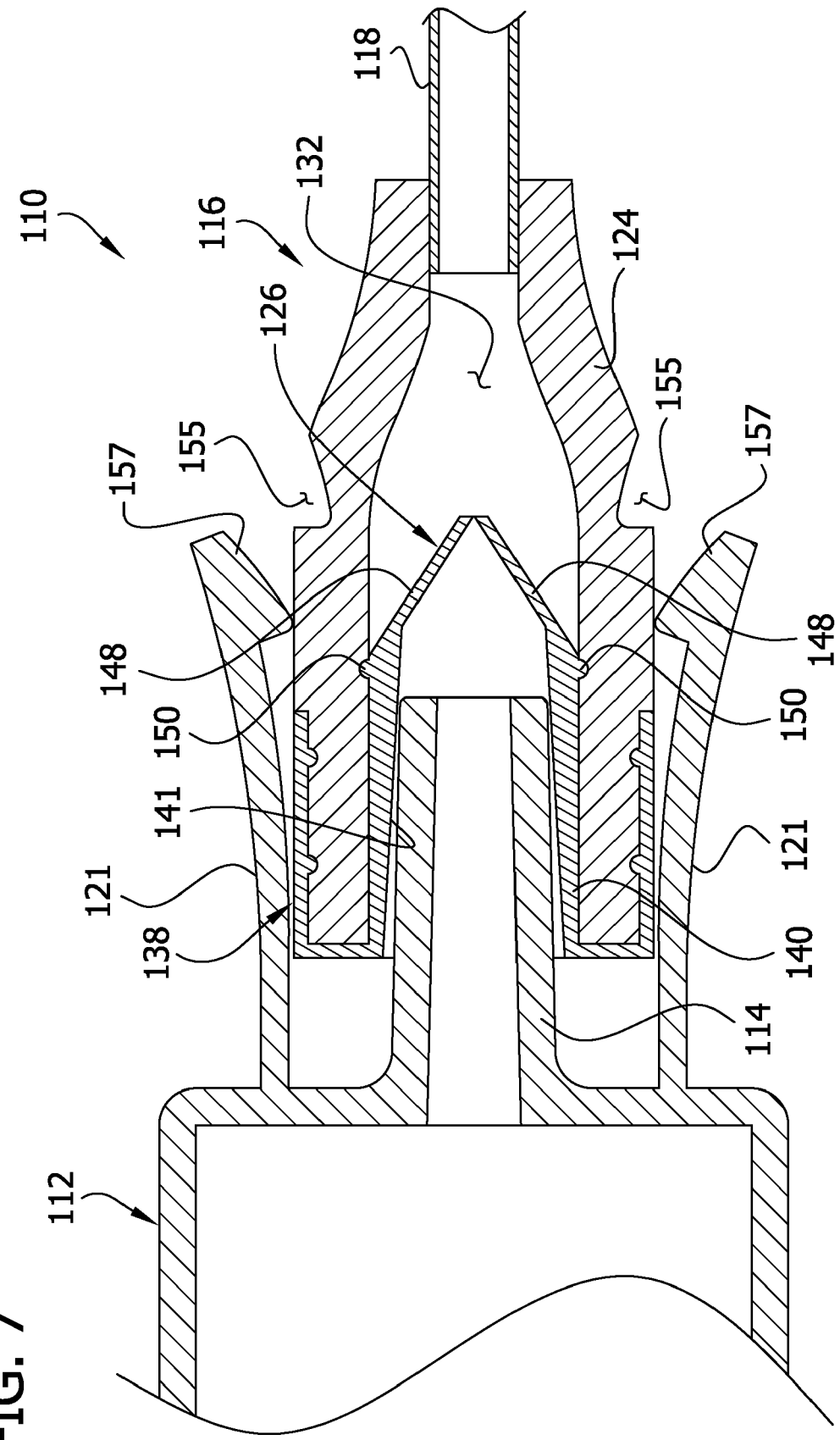
FIG. 7 is a sectional view of a second embodiment of an enteral feeding set with an oral tip syringe partially inserted in a female adaptor.
Figure 8:
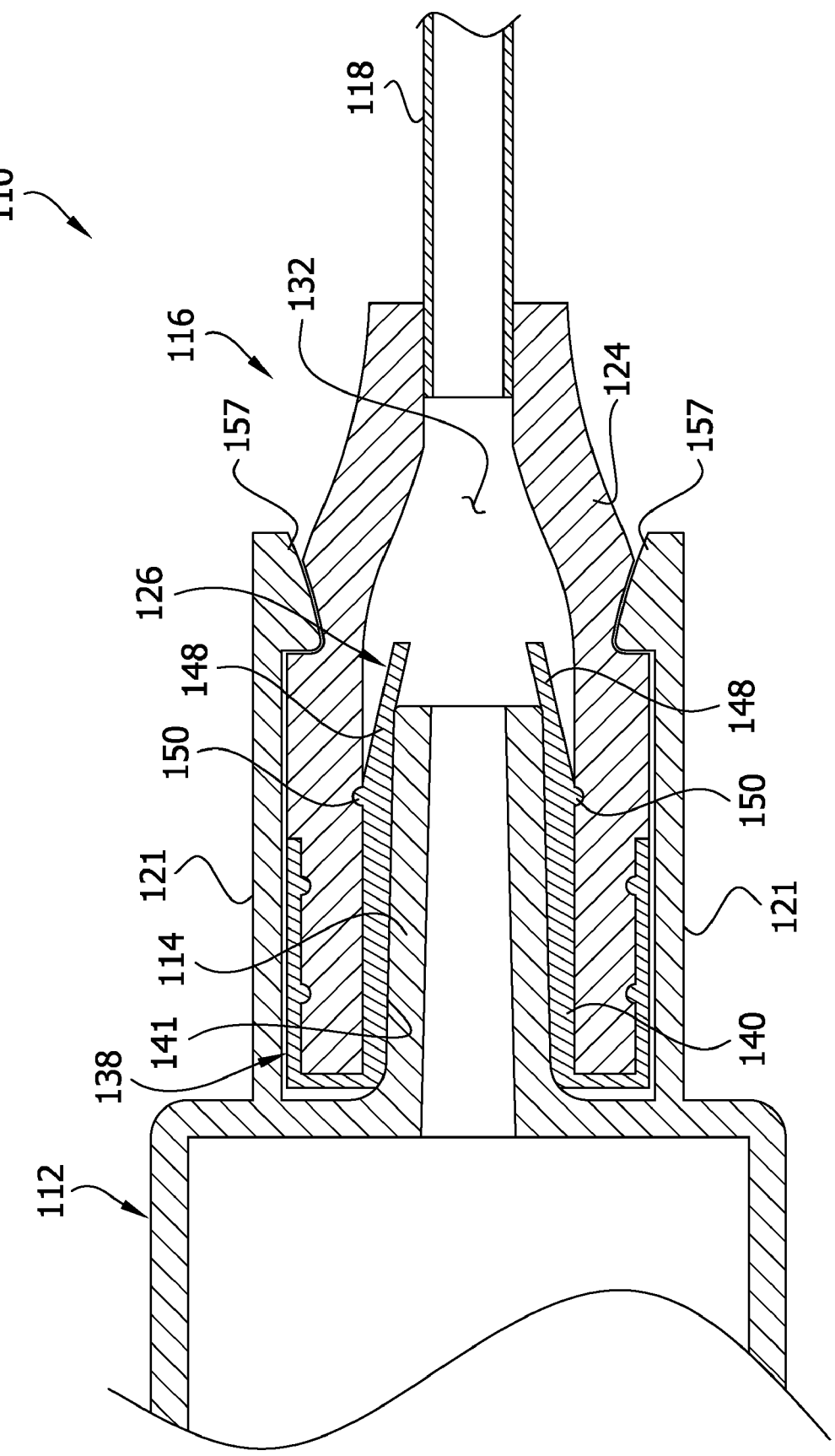
FIG. 8 is similar to FIG. 7 but with the oral tip syringe fully inserted into the female adaptor.

Referring to FIGS. 7 and 8, a second embodiment of the enteral feeding set is generally indicated at 110. This enteral feeding set 110 has components identical to the first embodiment, which are indicated by corresponding reference numerals plus 100. In general, the enteral feeding set 110 includes a syringe (broadly, a source of liquid enteral product), generally indicated at 112, comprising a barrel 113 and an oral tip 114 extending outward from the barrel. The feeding set 110 also includes a female adaptor, generally indicated at 116, secured to a feeding line comprising feeding tubing 118. Reference is made to the description above regarding the first embodiment for specific description of each of the identical components of the second enteral feeding set 110.

The difference between the first embodiment and the second embodiment is the securement mechanism for releasably securing the syringe 112 to the female adaptor 116. In particular, the securement mechanism of the second feeding set 110 includes male snap-fit components 121 that have barbs 157 extending inward toward the tip 114. The male snap-fit components 121 contact the exterior surface of the female adaptor 116 and elastically deflect outward as the tip 114 is inserted into the female adaptor, as shown in FIG. 7. Upon full insertion of tip 114 into the female adaptor 116 (FIG. 8), the barbs 157 snap into grooves 155 (broadly, female snap-fit components) formed in the outer surface of the female adaptor 116. Other ways of securing the syringe 121 to the female adaptor 116 do not depart from the scope of the present invention.

Throughout the drawings, the source of liquid enteral product is illustrated as a syringe because it is envisioned that the adaptor 10 will be used to deliver relatively small amounts of liquid enteral product to the patient. For example, the adaptor 10 may be used when delivering, via the oral-tip syringe 12, medicinal liquid into the feeding tubing 18. However, it is understood that the source of liquid enteral product may be devices other than syringes.

Having described embodiments of the invention in detail, it will be apparent that modifications and variations are possible without departing from the scope of the invention defined in the appended claims.

When introducing elements of the present invention or the preferred embodiments thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. An adaptor for discriminating connection of an oral tip having a length greater than 0.50 in. (12.70 mm) to a feeding line and for preventing sealed connection with a standard semi-rigid luer tip having a length less than or equal to 0.50 in (12.70 mm), the adaptor comprising:
    a body having first and second open ends and a passage for flow of fluid from the first end to the second end;
    an oral tip connector defining a connection port in the passage adjacent the first end of the body, the connection port being sized and shaped to sealingly receive the oral tip and to prevent sealing connection with the standard semi-rigid luer tip having a length less than or equal to 0.50 in (12.70 mm);
    a duckbill valve in the passage between the first and second open ends of the body, said duckbill valve comprising valve flaps that are biased toward a closed position in which the flaps are in sealing contact with one another at an apex of the valve to substantially seal the second open end of the body from the connection port, the duckbill valve being spaced at least 0.50 in (12.70 mm) downstream from the first open end of the body such that when the oral tip is fully inserted into the connection port, the oral tip engages the valve flaps and opens the valve, and when the standard semi-rigid luer tip is fully inserted into the connection port, the standard semi-rigid luer tip does not contact the valve flaps and the valve flaps remain in said closed position.

2. An adaptor as set forth in claim 1 wherein the oral tip connector is formed integrally with the duckbill valve as a one-piece component.

3. An adaptor as set forth in claim 1 wherein the oral tip connector includes an inner sealing member defining the connection port, and a skirt secured to the inner sealing member at the first open end of the body, the skirt having a radial portion overlying the first open end of the body and an axial portion surrounding an exterior surface of the body.

4. An adaptor as set forth in claim 3 wherein the duckbill valve, the inner sealing member, and the skirt are integrally formed as a generally elastic, one-piece component.

5. An adaptor as set forth in claim 4 wherein the body includes an exterior annular groove in an exterior surface of the body, wherein the skirt includes an O-ring on an interior surface of the skirt received in the exterior annular groove.

6. An adaptor as set forth in claim 1 further comprising a female snap-fit component on the body of the adaptor for snap-fit connection to male snap-fit components associated with the oral tip.

7. An adaptor as set forth in claim 6 wherein the female snap-fit component comprises a circumferential flange on the body of the adaptor, the flange having openings for receiving the male snap-fit components associated with the oral tip.

8. An adaptor as set forth in claim 6 wherein the female snap-fit component comprises a groove in the body of the adaptor for receiving the male snap-fit components associated with the oral tip.

9. An adaptor as set forth in claim 1 wherein the duckbill valve is spaced less than or equal to about 25.4 mm (1.0 in) downstream from the first open end of the body.

10. An adaptor as set forth in claim 1 wherein an end of the connection port adjacent to the duckbill valve has a minimum cross-sectional diameter greater than 4.027 mm (0.159 in).

11. A feeding administration set comprising:
an oral tip having a length greater than 0.50 in (12.70 mm); and
an adaptor comprising
a body having first and second open ends and a passage for flow of fluid from the first end to the second end,
an oral tip connector defining a connection port in the passage adjacent the first end of the body, the connection port being sized and shaped to sealingly receive the oral tip, and
a duckbill valve in the passage between the first and second open ends of the body, said duckbill valve comprising valve flaps that are biased toward a closed position in which the flaps are in sealing contact with one another at an apex of the valve to substantially seal the second open end of the body from the connection port, the duckbill valve being spaced downstream from the first open end of the body such that when the oral tip is fully inserted into the connection port, the oral tip engages the valve flaps and opens the valve, and when an oral tip having a length less than or equal to 0.50 in. is fully inserted into the connection port it will not engage the valve flaps to open the valve.

12. A feeding administration set as set forth in claim 11 wherein the oral tip connector is formed integrally with the duckbill valve as a one-piece component.

13. A feeding administration set as set forth in claim 12 wherein the oral tip connector includes an inner sealing member defining the connection port, and a skirt secured to the inner sealing member at the first open end of the body, the skirt having a radial portion overlying the first open end of the body and an axial portion surrounding an exterior surface of the body.

14. A feeding administration set as set forth in claim 13 wherein the duckbill valve, the inner sealing member, and the skirt are integrally formed as a generally elastic, one-piece component.

15. A feeding administration set as set forth in claim 14 wherein the body includes an exterior annular groove in an exterior surface of the body, wherein the skirt includes an O-ring on an interior surface of the skirt received in the exterior annular groove.

16. A feeding administration set as set forth in claim 11 wherein the syringe further comprises male snap-fit components extending outward from the barrel generally adjacent to the oral tip, and wherein the adaptor further comprises a female snap-fit component associated with the body for releasable, mateable connection with the male snap-fit components of the syringe.

17. A feeding administration set as set forth in claim 16 wherein the female snap-fit component includes a circumferential flange on the body of the adaptor, the flange having openings for receiving male snap-fit components associated with the oral tip.

18. An adaptor for connecting an oral tip to a feeding line, the adaptor comprising:
a tubular body having an exterior surface, first and second open ends and a passage for flow of fluid from the first end to the second end; and
an integrally formed, one-piece oral tip connector secured to the body, the oral tip connector including
an inner sealing member in the passage adjacent the first end of the body defining a connection port that is and shaped to sealingly receive the oral tip, the inner sealing member having first and second ends,
a skirt having a radial portion adjacent the first end of the sealing member and overlying the first open end of the body, and an axial portion surrounding the exterior surface of the body,
a duckbill valve adjacent the second end of the inner sealing member in the passage between the first and second open ends of the body, said duckbill valve comprising valve flaps that are biased toward a closed position in which the flaps are in sealing contact with one another at an apex of the valve to substantially seal the second open end of the body from the connection port, the duckbill valve being spaced downstream from the first open end of the body such that when the oral tip is fully inserted into the connection port, the oral tip contacts the valve flaps and opens the valve.

19. An adaptor as set forth in claim 18 wherein the exterior surface of the body defines an annular recess, the axial portion of the skirt being received in the annular recess so that an outer surface of the skirt is generally flush with the exterior surface of the body adjacent the recess.

20. An adaptor as set forth in claim 19 wherein the exterior surface of the body defines annular grooves, and wherein the axial portion of the skirt has spaced apart O-rings received in the annular grooves.

* * * * *